(12) United States Patent
Akahoshi

(10) Patent No.: US 7,601,136 B2
(45) Date of Patent: Oct. 13, 2009

(54) INFUSION SLEEVE

(76) Inventor: Takayuki Akahoshi, 1-11-7-2603, Tsukuda, Chuoku, Tokyo (JP) 104-0051

( * ) Notice: Subject to any disclaimer, the term of this patent is extended or adjusted under 35 U.S.C. 154(b) by 254 days.

(21) Appl. No.: 11/320,105

(22) Filed: Dec. 28, 2005

(65) Prior Publication Data

US 2006/0100653 A1 May 11, 2006

Related U.S. Application Data

(63) Continuation-in-part of application No. 11/069,772, filed on Mar. 1, 2005.

(60) Provisional application No. 60/589,638, filed on Jul. 20, 2004.

(51) Int. Cl.
*A61F 9/007* (2006.01)

(52) U.S. Cl. ....................................................... 604/22

(58) Field of Classification Search .................. 604/274, 604/22, 27, 264; 606/107
See application file for complete search history.

(56) References Cited

U.S. PATENT DOCUMENTS

| | | | | |
|---|---|---|---|---|
| 4,643,717 A * | 2/1987 | Cook et al. | ............... | 604/22 |
| 4,808,154 A * | 2/1989 | Freeman | ............... | 604/22 |
| 5,084,009 A * | 1/1992 | Mackool | ............... | 604/22 |
| 5,151,084 A * | 9/1992 | Khek | ............... | 604/22 |
| 5,256,147 A * | 10/1993 | Vidal et al. | ............... | 604/158 |
| 5,286,256 A * | 2/1994 | Mackool | ............... | 604/22 |
| 5,334,169 A * | 8/1994 | Brown et al. | ............... | 604/527 |
| 5,354,265 A * | 10/1994 | Mackool | ............... | 604/22 |
| 5,505,693 A * | 4/1996 | Mackool | ............... | 604/22 |
| 5,520,193 A * | 5/1996 | Suzuki et al. | ............... | 600/577 |
| 5,533,957 A * | 7/1996 | Aldea | ............... | 600/16 |
| 5,597,377 A * | 1/1997 | Aldea | ............... | 600/16 |
| 5,634,912 A * | 6/1997 | Injev | ............... | 604/264 |
| 5,645,530 A * | 7/1997 | Boukhny et al. | ............... | 604/22 |
| 5,685,841 A * | 11/1997 | Mackool | ............... | 604/22 |
| 5,718,676 A * | 2/1998 | Barrett | ............... | 604/22 |
| 5,725,495 A * | 3/1998 | Strukel et al. | ............... | 604/44 |
| 5,873,851 A * | 2/1999 | Nilsson | ............... | 604/43 |
| 5,879,356 A * | 3/1999 | Geuder | ............... | 606/107 |
| 5,919,157 A * | 7/1999 | Strukel | ............... | 604/22 |
| 5,935,096 A * | 8/1999 | Barrett | ............... | 604/22 |
| 5,989,209 A * | 11/1999 | Barrett | ............... | 604/22 |
| 6,033,376 A * | 3/2000 | Rockley | ............... | 604/22 |
| 6,117,151 A * | 9/2000 | Urich et al. | ............... | 606/169 |
| 6,159,175 A * | 12/2000 | Strukel et al. | ............... | 604/22 |
| 6,299,591 B1 * | 10/2001 | Banko | ............... | 604/22 |
| 6,428,501 B1 * | 8/2002 | Reynard | ............... | 604/27 |

(Continued)

*Primary Examiner*—Nicholas D Lucchesi
*Assistant Examiner*—Aarti Bhatia
(74) *Attorney, Agent, or Firm*—Jerry A. Schulman

(57) ABSTRACT

An infusion sleeve for use with a phacoemulsification handpiece has a hollow body with an open end by which the sleeve is attachable to the handpiece and an open tip through which a phacoemulsification needle is passed. Irrigating liquid is directed from the handpiece through the sleeve. At least three discharge ports are formed in the sleeve to provide increased flow of irrigating liquid proximate the sleeve tip. The ports may differ in size, shape and positioning on the sleeve. Internal reinforcing ribs are provided to limit contact between the thinner portions of the sleeve wall and the phacoemulsification needle. External ridges are provided to limit leakage through the incision. A sleeve with an oval cross-sectional configuration is also provided to limit leakage through the incision. These features may be combined to provide sleeves with desired characteristics.

11 Claims, 8 Drawing Sheets

U.S. PATENT DOCUMENTS

| | | | |
|---|---|---|---|
| 6,605,054 B2 * | 8/2003 | Rockley | 604/22 |
| 6,830,555 B2 * | 12/2004 | Rockley et al. | 604/22 |
| 7,014,629 B2 * | 3/2006 | Mackool | 604/274 |
| 7,094,229 B2 * | 8/2006 | Boukhny et al. | 604/500 |
| 2001/0034504 A1 * | 10/2001 | Zaleski | 604/164.12 |
| 2003/0004455 A1 * | 1/2003 | Kadziauskas et al. | 604/27 |
| 2004/0153026 A1 * | 8/2004 | Mackool | 604/22 |
| 2005/0277897 A1 * | 12/2005 | Ghannoum et al. | 604/264 |
| 2008/0300531 A1 * | 12/2008 | Gills, Jr. | 604/22 |

* cited by examiner

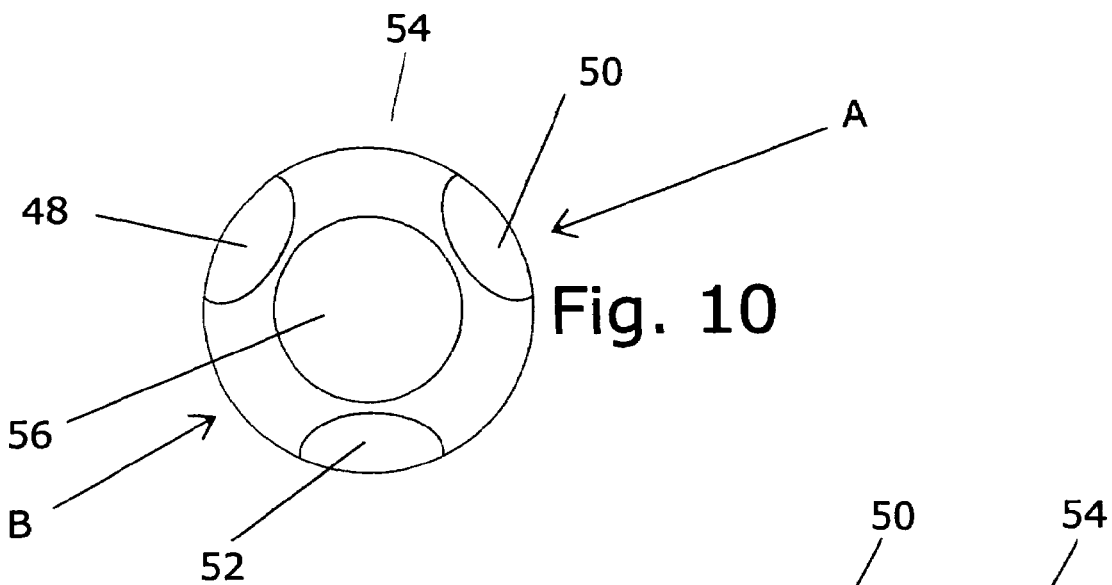
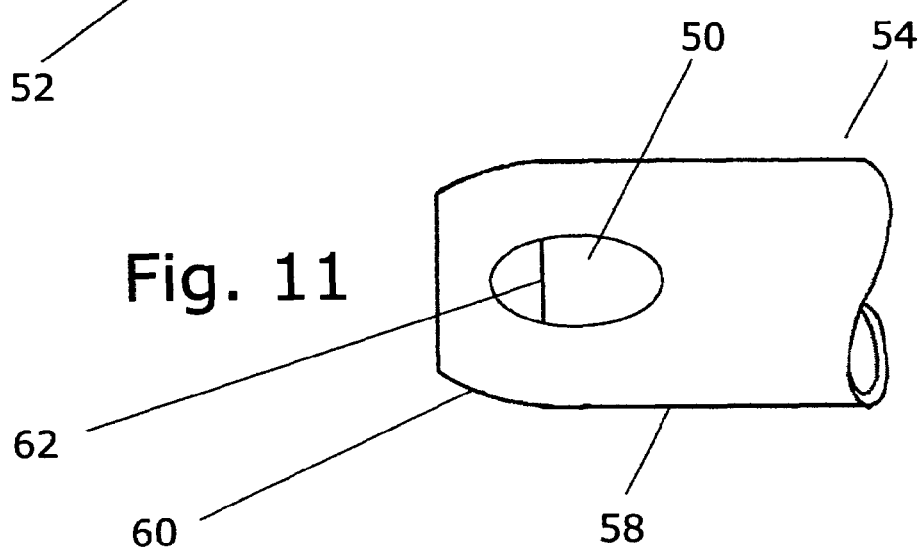
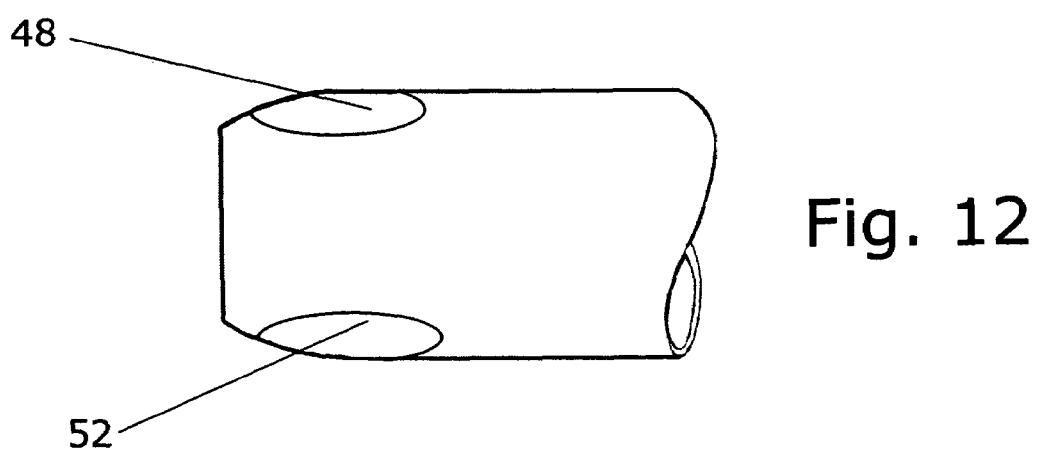

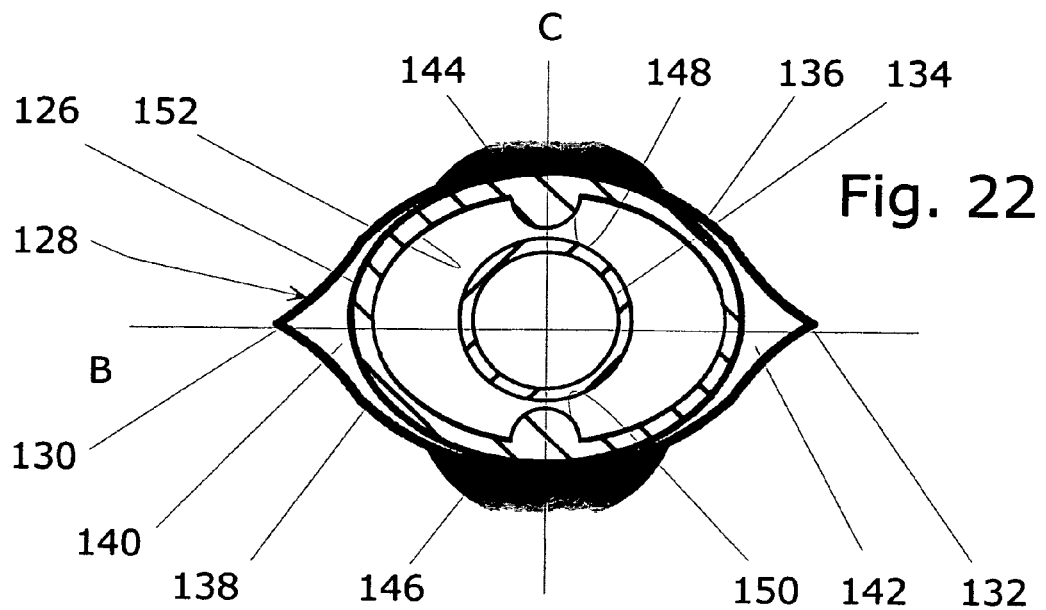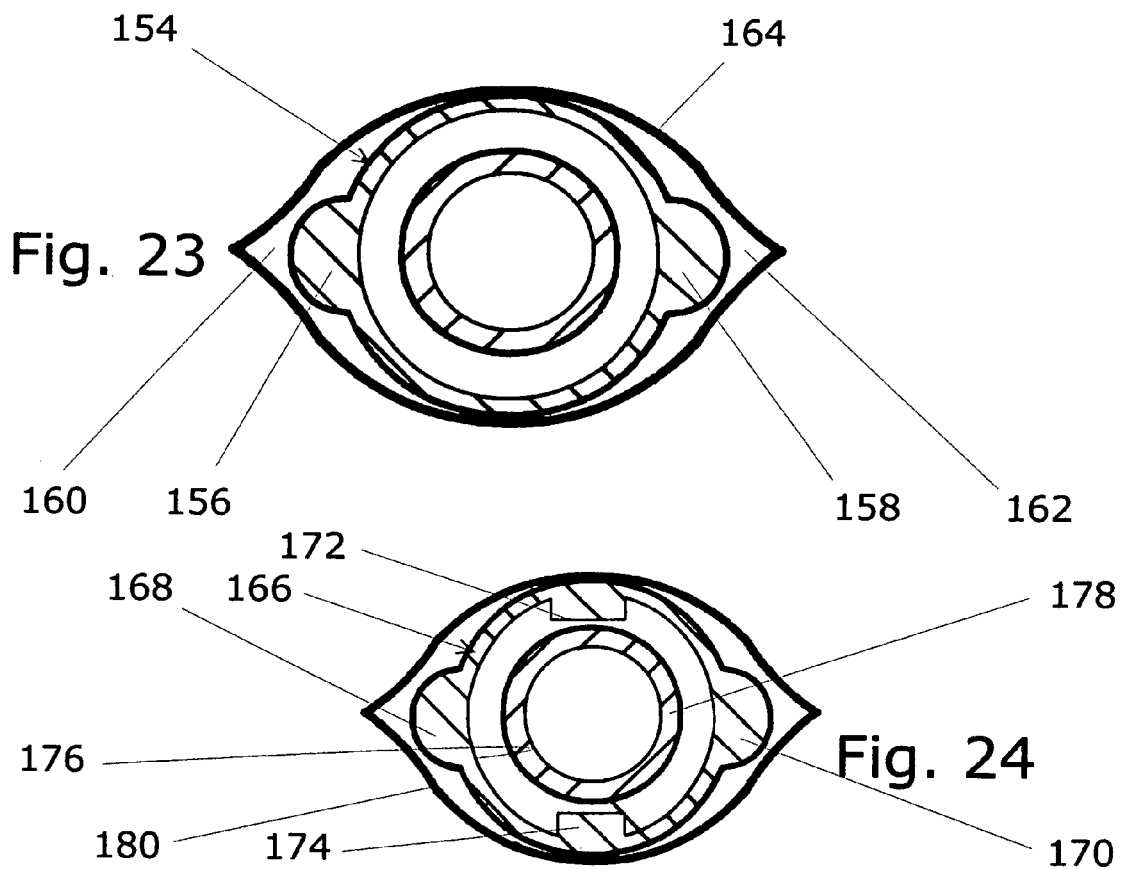

INFUSION SLEEVE

This invention relates to surgical instruments and surgical techniques used in eye surgery and more particularly, to the technique of phacoemulsification apparatus and methods for their use. This is a continuation-in-part application of application Ser. No. 11/069,772, filed Mar. 1, 2005 which claims priority from provisional application Ser. No. 60/589,638, filed Jul. 20, 2004.

BACKGROUND OF THE INVENTION

A common ophthalmological surgical technique is the removal of a diseased or injured lens from the eye. Earlier techniques used for the removal of the lens typically required a substantial incision to be made in the capsular bag in which the lens is encased. Such incisions were often on the order of 12 mm in length.

Later techniques focused on removing diseased lenses and inserting replacement artificial lenses through as small an incision as possible. For example, it is now a common technique to take an artificial intraocular lens (IOL), fold it and insert the folded lens through the incision, allowing the lens to unfold when it is properly positioned within the capsular bag. Similarly, efforts have been made to accomplish the removal of the diseased lens through an equally small incision.

One such technique is known as phacoemulsification. A typical phacoemulsification tool includes a hollow needle to which electrical energy is applied to vibrate the needle at ultrasonic frequencies in order to fragment the diseased lens into small enough particles to be aspirated from the eye. Commonly, an infusion sleeve is mounted around the needle to supply irrigating liquids to the eye in order to aid in flushing and aspirating the lens particles.

It is extremely important to properly infuse liquid during such surgery. Maintaining a sufficient amount of liquid prevents collapse of certain tissues within the eye and attendant injury or damage to delicate eye structures. As an example, endothelial cells can easily be damaged during such collapse and this damage is permanent because these cells do not regenerate. One of the benefits of using as small in incision as possible during such surgery is the minimization of leakage of liquid during and after surgery and the prevention of such a collapse One way to ensure infusion of a sufficient amount of liquid within the eye during an operation is to increase liquid flow through the infusion sleeve. This can cause an increase in the Reynolds number of the infusion liquid to the point where the liquid flow become turbulent which can, in itself cause damage to the eye.

Instruments using various types of infusing sleeves are well known and well-represented in the art and exemplify the attempts made by others to address the problem of maintaining an adequate flow of irrigating liquid without causing damage to the eye.

U.S. Pat. No. 4,643,717 (Cook et al) teaches and describes an aspiration fitting adapter formed as a sleeve concentric to the phaco needle and having a pair of bilaterally opposed discharge ports formed proximate the end of the sleeve to infuse irrigating liquid into the eye.

U.S. Pat. No. 5,151,084 (Khek) teaches and describes an ultrasonic needle with an infusion sleeve that includes a baffle. The sleeve of Khek also fits concentrically about the needle and allows the needle to protrude a substantial distance therefrom while providing pair of discharge ports bilaterally opposed to each other near the terminus of the sleeve.

U.S. Pat. No. 6,117,151 (Urich et al) teaches and describes an eye incision temperature protection sleeve fitted concentrically about a needle and having a single discharge port through which irrigating liquid is passed.

U.S. Pat. No. 6,605,054 (Rockley) teaches and describes a multiple bypass port phaco tip having multiple aspiration ports and a single discharge port to infuse liquid into the eye.

U.S. Pat. No. 5,879,356 (Geuder) teaches and describes a surgical instrument for crushing crystalline eye lenses by means of ultrasound and for removing lens debris by suction which demonstrates the use of a sleeve positioned concentric to the needle and having a pair of discharge ports formed thereon.

A series of patents issued to Richard J. Mackool illustrates further variations of irrigating sleeves. Mackool forms the sleeve with a somewhat flattened cross-section configuration intended to more closely approximate the shape of the incision through which the sleeve is inserted into the eye. This cross-section can be seen at FIG. 3 of U.S. Pat. No. 5,084,009.

U.S. Pat. No. 5,084,009 (Mackool) teaches and describes a liquid infusion sleeve for use during eye surgery with the sleeve having a flattened cross-section and having a pair of infusion ports formed on the forward portion of the flattened section.

U.S. Pat. No. 5,286,256 (Mackool) teaches and describes a liquid infusion sleeve having a free-floating rigid sleeve surrounding a needle which is intended to prevent the outer flexible sleeve from collapsing onto the needle.

U.S. Pat. No. 5,354,265 (Mackool) teaches and describes a liquid infusion sleeve showing yet another construction intended to keep the outer flexible infusion sleeve from collapsing onto the vibrating needle.

U.S. Pat. No. 5,505,693 (Mackool) teaches and describes a method and apparatus for reducing friction and heat generation by an ultrasonic device during surgery incorporating a needle support to prevent collapse of the outer flexible sleeve.

The Mackool patents are characterized by a pair of discharge ports formed at the distal end of the sleeve through which irrigating liquid is passed into the eye during the operation.

U.S. Pat. No. 5,645,530 (Boukhny) teaches and describes a phaco emulsification sleeve, one variation of which has a bellows portion attached to a discharge port ring which directs an annular flow of liquid around the needle and into the eye. The use of the bellows is intended to allow the sleeve to absorb spikes in liquid pressure during the operation.

U.S. Pat. No. 5,634,912 (Injev) teaches and describes an infusion sleeve having a rotating tip to allow the phaco needle to be repositioned during surgery. The top also has a single discharge port for infusing liquid during surgery.

Published U.S. Patent Application No. 2003/0004455 (Kadziauskas) teaches and describes a bi-manual phaco needle using separate emulsification and aspiration needles inserted into the eye simultaneously during surgery.

While the foregoing references describe the problems faced during phaco emulsification with respect to supplying the eye with an adequate amount of irrigating liquid, they do not particularly point out nor describe apparatus nor methods for safely increasing the flow of liquid without attendant side effects. Accordingly, the need exists for an improved infusion sleeve which allows for a greater volume of liquid to be infused into the eye while avoiding the problems described in the prior art with respect to increased pressure, turbulence and the like.

The need also exists for such improved infusion sleeves to be simple in construction, efficient in operation and economical to manufacture.

In accordance with a preferred embodiment of the present invention, a phaco infusion sleeve has at least three infusion liquid discharge ports formed proximate the tip of the sleeve. In another embodiment, four such ports are formed equidistantly about the circumference of the sleeve and are oval in shape with the major axis of the oval parallel to the major axis of the sleeve. In another embodiment, three such ports are formed equidistantly about the circumference of the sleeve and staggered such that some ports are closer to the tip end than others and at least some of the ports are oval with the major axis of each oval substantially parallel to the major axis of the sleeve. Another embodiment includes ports spaced in a non-equidistant configuration. Another embodiment includes a series of internally-formed ribs along the inner surface of the sleeve.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further aspects of the present invention will become apparent upon consideration of the accompanying drawing figures in which:

BRIEF DESCRIPTION OF THE DRAWINGS

FIG. 10 is an end view of a second embodiment of the present invention showing three equidistantly spaced discharge ports;
FIG. 11 is a lateral view of a portion of the sleeve shown in FIG. 10;
FIG. 12 is a bottom view of a portion of the sleeve shown in FIG. 10;
FIG. 22 is a sectional view of an oval sleeve having internally-formed ribs and positioned within an incision;
FIG. 23 is a sectional view of a round sleeve having externally-formed ridges and positioned within an incision;
and
FIG. 24 is a sectional view of a round sleeve having both internally- and externally-formed ridges and positioned within an incision.

DETAILED DESCRIPTION OF THE DRAWINGS

Figure 1:
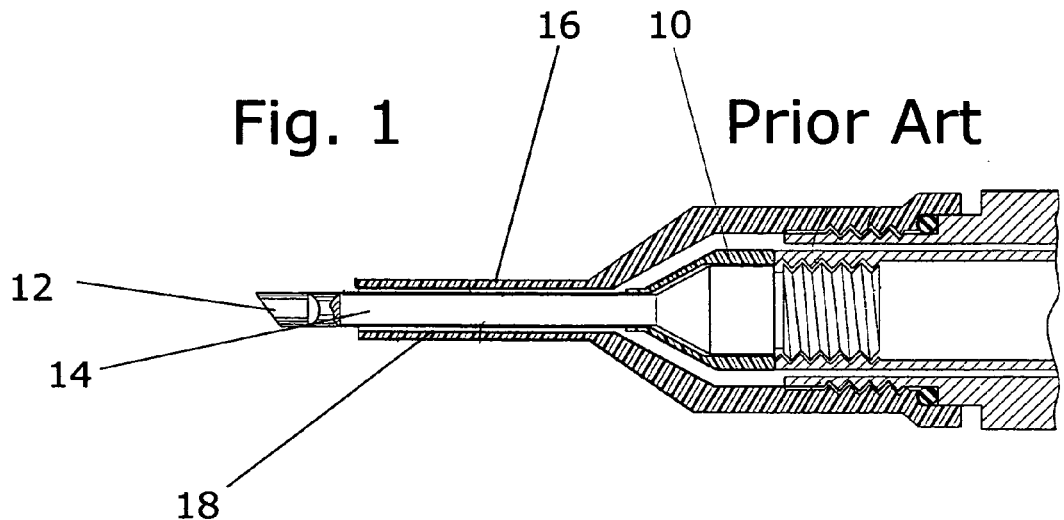
FIG. 1 is a first prior art illustration of an irrigation sleeve.

Referring now to FIG. 1 the numeral 10 indicates generally a partial sectional view of a prior art phacoemulsification hand piece having a needle 12 defining a hollow internal chamber 14 through which irrigation liquid and emulsified particles of a lens are aspirated from the capsular bag. As seen in FIG. 1, an irrigating sleeve 16 is mounted to hand piece 10, from which needle 12 protrudes. Sleeve 16 communicates with an irrigation liquid supply within handpiece 10 and provides irrigating liquid to the capsular bag through an annular channel 18 formed between needle 12 and sleeve 16.

Figure 2:
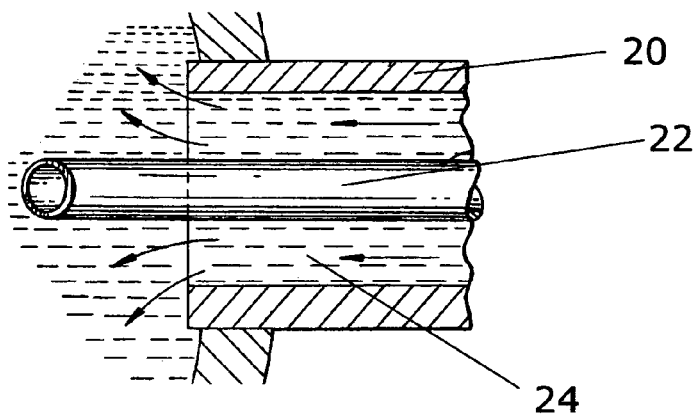
FIG. 2 is a second illustration of a prior art irrigation sleeve.

Referring now to FIG. 2, an enlarged partial sectional view of a second prior art phacoemulsification apparatus is shown having a sleeve 20 surrounding a hollow needle 22 and defining therebetween an annular channel 24 as a conduit for irrigating liquid.

Both FIG. 1 and FIG. 2 show a prior art apparatus with the flow of irrigating liquid directed annularly about the periphery of the hollow phaco needle.

Figure 3:
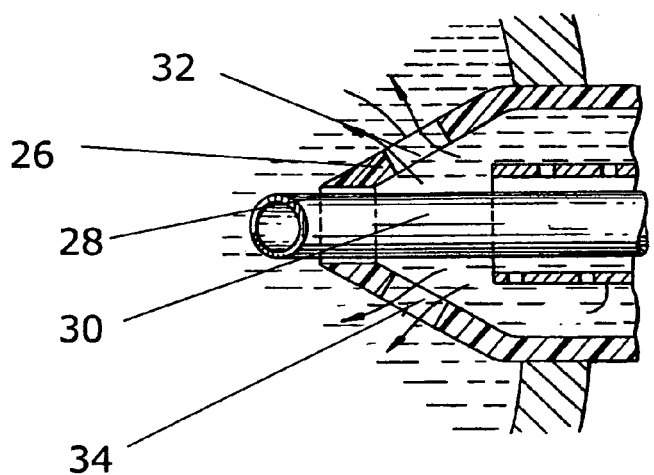
FIG. 3 is a third illustration of a prior art irrigation sleeve.

Referring now to FIG. 3, a partial sectional view of a second embodiment of the apparatus of FIG. 2 is shown where the infusion sleeve 26 tapers to form an opening 28 through which needle 30 extends. A pair of infusion ports 32, 34 are formed in the angled side walls of sleeve 26 to form a pathway for infusing liquid.

The embodiments shown in FIGS. 2 and 3 are taken from U.S. Pat. No. 5,084,009 and as discussed above, it appears that ports 32, 34 are formed along the flattened portion of sleeve 26 and are the only infusion ports present.

I have found, surprisingly, that the addition of one or more infusion ports results in a higher flow rate of infusing liquid without causing problems of damage to cellular structures within the eye such as the endothelial cells and which preserves the desirable flow characteristics of the infusing liquid. I have also found that a higher flow rate under these flow conditions provides additional unexpected benefits. For example, the flow from an additional port may be directed to stretch and deepen the capsular bag, decreasing the risk of posterior capsule rupture.

FIGS. 4-18 demonstrate the modifications and variations to an existing phaco infusion sleeve. For purposes of clarity, only the tip portion of each such sleeve will be shown, it being understood that the sleeve is fitted coaxial to a phaco needle which extends outward from the sleeve.

Figure 4:
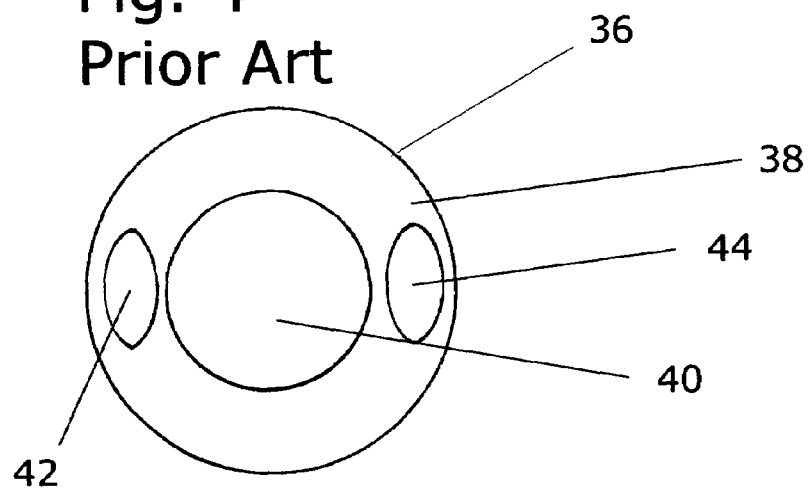
FIG. 4 is an end view of an irrigation sleeve having two circular and bilaterally opposed discharge ports.

FIG. 4 is an end view of a known prior art infusion sleeve having an outer sleeve wall 36, a curved sleeve wall portion 38 which is the terminus for a central passage 40 to accommodate the phaco needle and a pair of diametrically opposed infusion ports 42, 44. This is the present arrangement on currently available infusion sleeves.

Figure 5:
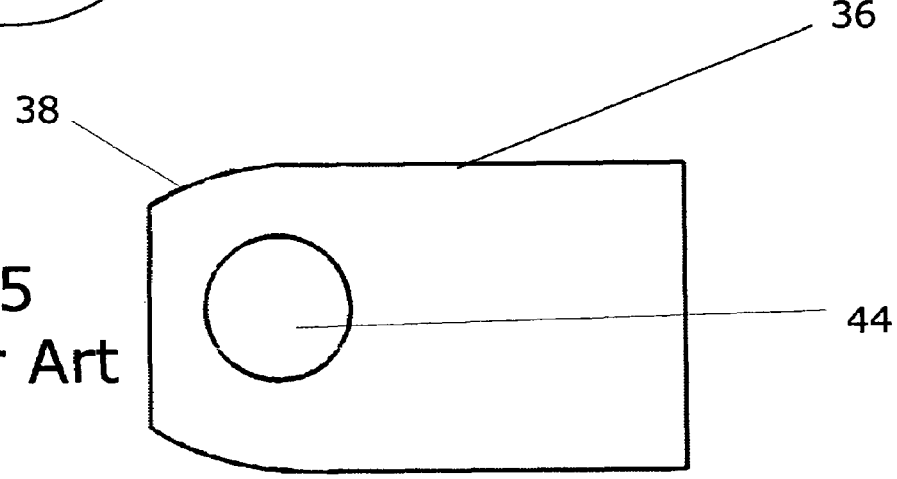
FIG. 5 is a lateral view of a portion of the sleeve shown in FIG. 4.
Figure 6:
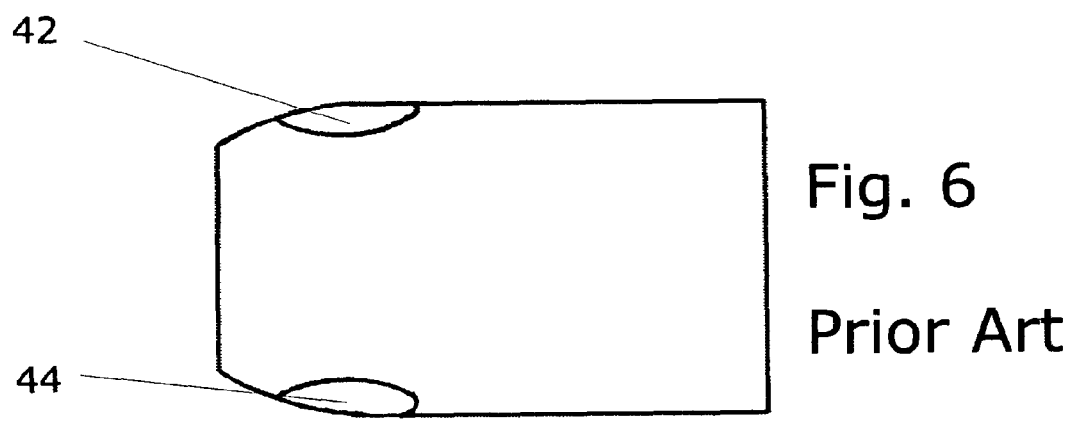
FIG. 6 is a top view of a portion of the sleeve shown in FIG. 4.

FIG. 5 is a lateral side view of the sleeve tip shown in FIG. 4, demonstrating that the infusion port 44 is circular in shape. FIG. 6 is a top view of the tip of FIG. 4 again demonstrating the diametrically opposed positions of infusion ports 42, 44.

Figure 7:
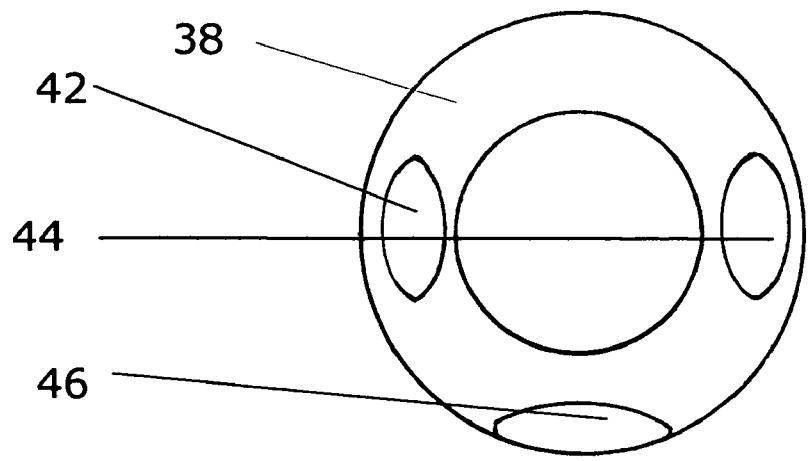
FIG. 7 is an end view of a modified version of the sleeve shown in FIG. 6.
Figure 8:
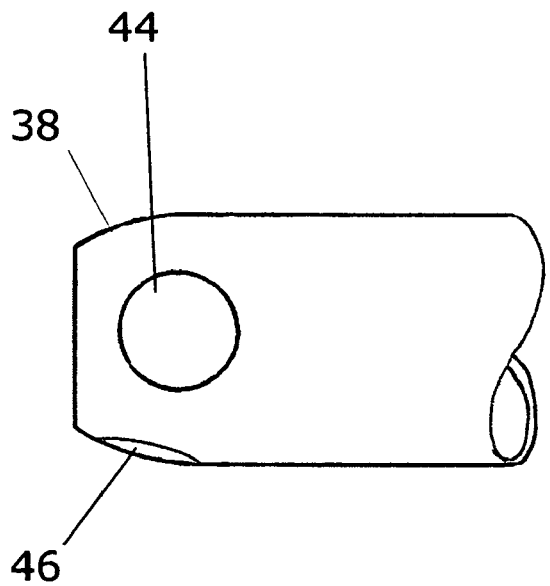
FIG. 8 is a lateral view of a portion of the sleeve shown in FIG. 7.
Figure 9:
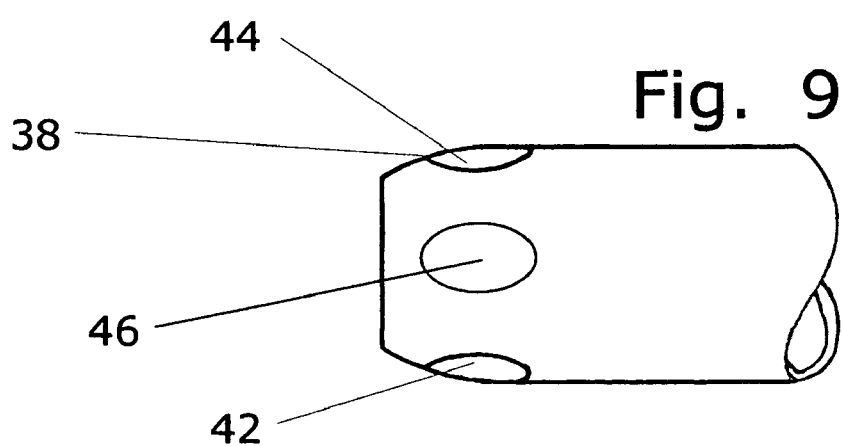
FIG. 9 is a bottom view of a portion of the sleeve shown in FIG. 7.

Referring to FIG. 7, a first embodiment of the present invention is shown wherein the tip of FIG. 4 has been modified to add a third infusion port 46 together with ports 42 and 44. In this embodiment, infusion port 46 is oval in shape as can be seen in FIG. 9, is positioned midway between infusion ports 42 and 44 and as shown in FIGS. 7 and 9, is positioned with ports 42 and 44 on curved sleeve portion 38. FIG. 8 shows the position of infusion port 46 in a lateral view.

Referring now to FIGS. 10, 11 and 12, a second preferred embodiment is shown wherein infusion ports 48, 50, 52 are positioned equidistantly about the periphery of sleeve 54 and communicate with tip channel 56. FIG. 11 is a view taken in direction A as shown in FIG. 10, demonstrating the oval shape of infusion port 50. FIG. 12 is a view taken along direction B of FIG. 10 demonstrating the positioning and oval shape of infusion ports 48, 52.

As seen most clearly in FIG. 11, one portion of port 50 is formed through a straight portion 58 of sleeve 54 while a second portion is formed along the tapering section 60 of sleeve 54. A portion of port 50 is thus angled, at break line 62. This has the effect of directing a portion of the flow passing through port 50 away from the aspiration zone at the tip of the needle while allowing for a greater volume of infusion liquid to pass through at an even flow rate.

Figure 13:
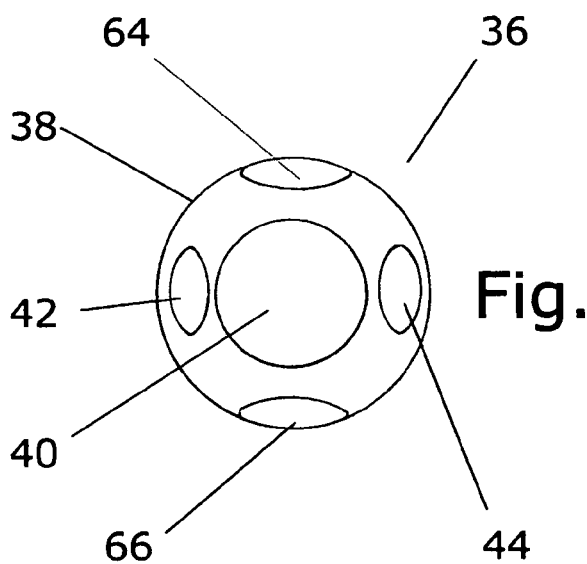
FIG. 13 is an end view of the sleeve of FIG. 4 modified to include four discharge ports.
Figure 14:
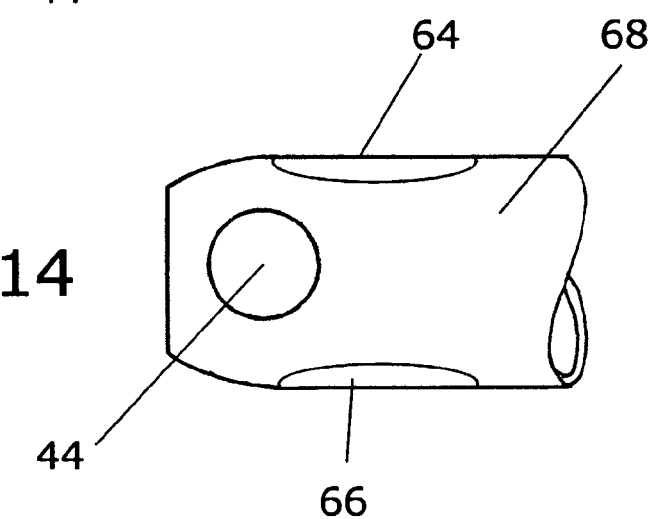
FIG. 14 is a lateral view of a section of the sleeve shown in FIG. 13.
Figure 15:
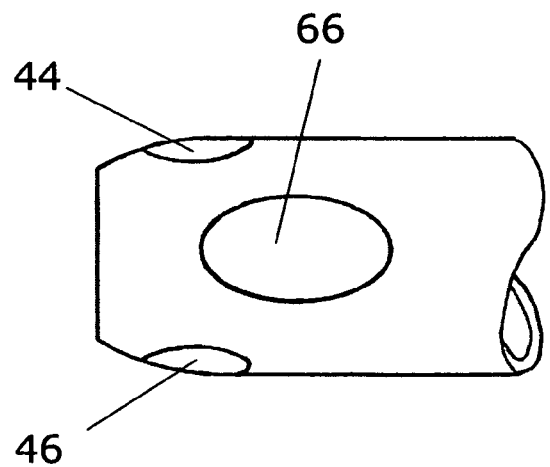
FIG. 15 is a top view of a portion of the sleeve shown in FIG. 13.

Referring now to FIGS. 13, 14 and 15, the fourth embodiment of the present invention is shown wherein an infusion sleeve of FIG. 4 is modified to add a pair of diametrically opposed infusion ports 64, 66. Infusion ports 64, 66 communicate with channel 40. As seen in FIG. 13, ports 42, 66, 44 and 64 are positioned equidistantly about the outer periphery of sleeve 36.

As seen in FIG. 14, infusion ports 64, 66 are positioned along the straight portion 68 of sleeve 36 and, as seen more clearly in FIG. 15, ports 64 and 66 are oval in shape.

Figure 16:
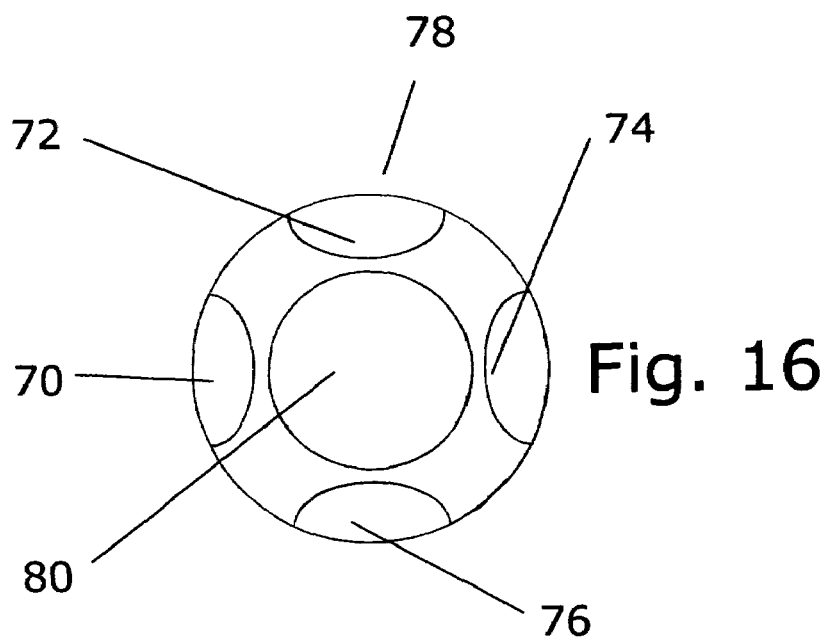
FIG. 16 is an end view of the embodiment of the present invention showing four oval discharge ports.
Figure 17:
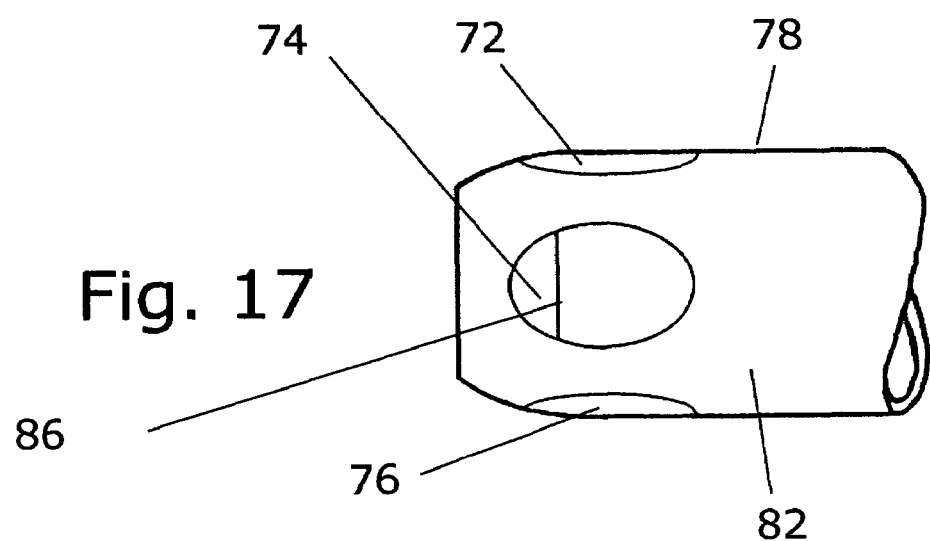
FIG. 17 is a lateral view of a portion of the sleeve shown in FIG. 16.
Figure 18:
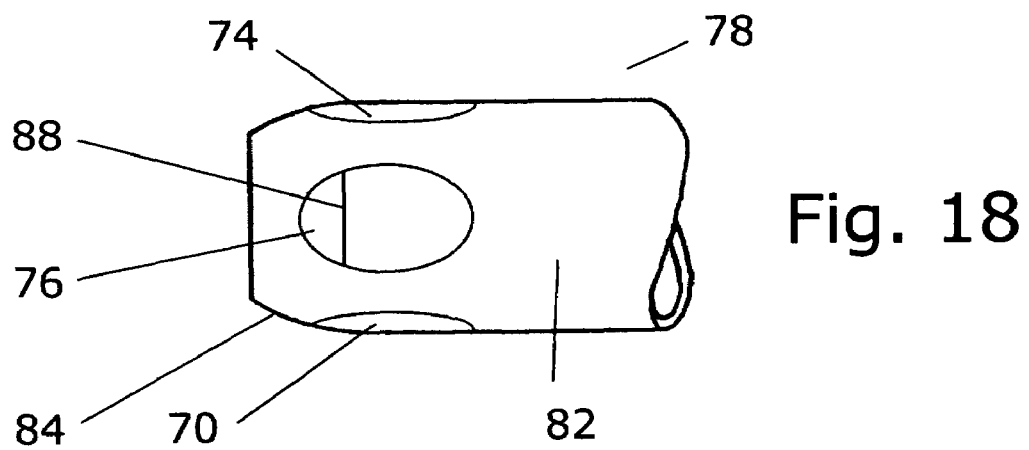
FIG. 18 is a top view of a portion of the sleeve shown in FIG. 16.

Referring now to FIGS. 16, 17 and 18, a fifth embodiment of the present invention is shown wherein a series of oval infusion ports 70, 72, 74 and 76 are positioned equidistantly about the periphery of sleeve 78. Each port 72, 74, 76 and 78 communicates with channel 80 of sleeve 78. As seen in FIG. 17, infusion port 74 is partially formed along a straight portion of straight portion 82 of sleeve 78 while the remaining portion is formed along a tapered portion 84 of sleeve 78, with port 74 angled at bend 86.

In like fashion, FIG. 18 shows that infusion port 76 is oval in shape and a portion of port 78 is formed on straight portion 82 of sleeve 78 while the remaining portion is formed through tapered portion 84 of sleeve 78, along bend 88.

Figure 19:
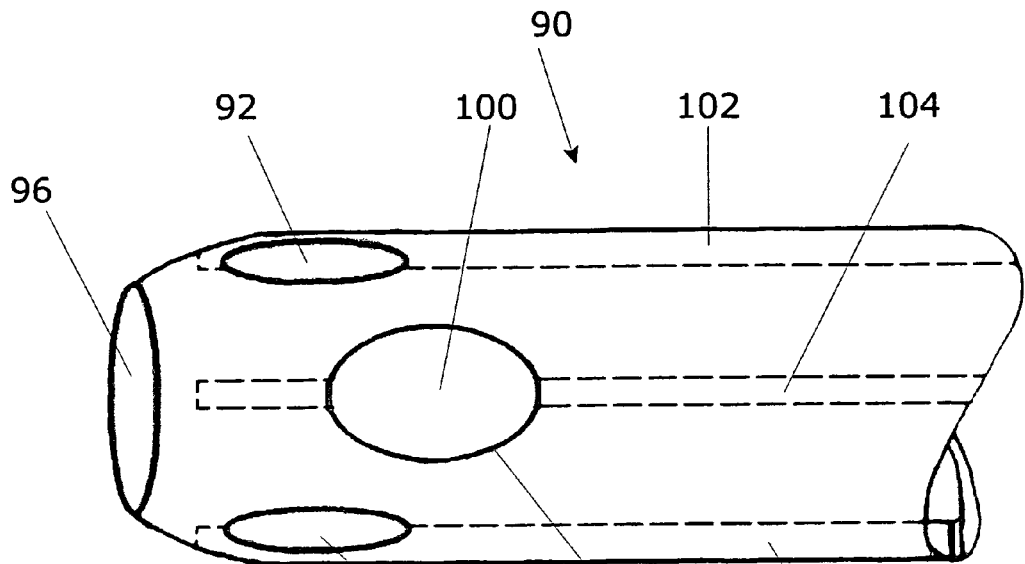
FIG. 19 is lateral view of a sleeve including internal ribs.

Referring now to FIG. 19, the numeral 90 identifies a microtip having ports 92 and 94 formed proximate channel 96 and with a pair of oppositely disposed ports 98, 100 which, in FIG. 19, coincide in the view shown. Preferably, ports 98, 100 are located farther distance away from the opening of channel 96 than are ports 92, 94.

In this preferred embodiment, ports 92, 94 are located 0.40 mm from the opening of channel 96. Channel 96 is round and is 1.35 mm in diameter while ports 92, 94 are round and are 1.10 mm in diameter. Preferably, ports 98, 100 are oval and are 1.10 by 1.30 mm with the 1.30 major axis being parallel to the major axis of tip 90.

Figures 20, 21:
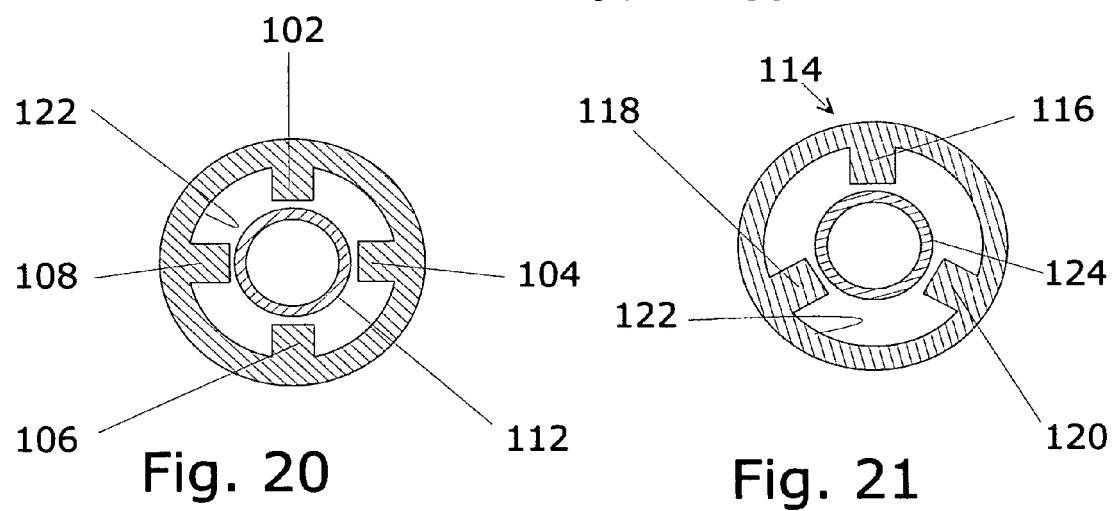
FIG. 20 is a view along line 20-20 of FIG. 19.
FIG. 21 is a sectional view showing an alternate arrangement of internal ribs.

The embodiment shown in FIG. 19 includes reinforcing internal ribs 102, 104, 106 and 108 which are intended to prevent collapse of tip 90 against needle 112 during phacoemulsification. internal ribs 102, 104, 106 and 108 can extend past ports such as 92 because the ports are formed after the internal ribs are molded and when the ports are punched or cut, the corresponding internal rib section will be removed along with the cutting. As seen in FIG. 20 said internal ribs are spaced equidistantly about the inner surface 110 of tip 90.

As seen in FIG. 20, internal ribs 102, 104, 106 and 108 extend toward phaco needle 112 and touch tip 90 to keep inner surface 122 from collapsing against needle 124.

While FIGS. 19 and 20 show four such internal ribs, it is to be understood that other arrangements and number of internal ribs can be selected as desired. As an example, in FIG. 21, tip 114 is shown having internal ribs 116, 118 and 120 formed equidistantly about the inner periphery and along the inner surface 122 of tip 114 and surrounding phacoemulsificaton needle 124.

It is also to be understood that the remaining tip configurations shown variously in FIGS. 7-18, may also if desired, include reinforcing internal ribs such as those shown in FIG. 19, FIG. 20 and FIG. 21.

The foregoing disclosures concerning the inclusion of ports in the sleeves shown in FIGS. 7-21 and as described above are also incorporated into a phacoemulsification sleeve having an oval cross-sectional shape, with certain variations.

Referring now to FIG. 22, the numeral 126 identifies a phacoemulsification sleeve having an oval cross-sectional configuration, with the sleeve section having a major, or longer axis B and a minor, or shorter axis C. FIG. 22 also illustrates the insertion of sleeve 126 through a linear incision 128 beginning at a first end 130 and terminating at a second end 132. Incision 128 is shown in the bowed or distended shape it acquires when an instrument such as a phacoemulsification handpiece needle 134 is inserted, forming an upper lip 136 and a lower lip 138.

The oval shape of sleeve 126 is intended to more closely approximate the distended shape of incision 128 as defined by upper and lower lips 136, 138 More particularly, the shape of sleeve 126 is intended to minimize the spaces 140, 142 that are formed at the corners of incision 128 when sleeve 126 is inserted. Minimizing spaces 140, 142 minimizes leakage through incision 128 while infusion is taking place during phacoemulsification.

As seen in FIG. 22, when sleeve 126 is inserted, major axis C of sleeve 126 is aligned with incision 128, while minor axis D is oriented generally perpendicular to incision 128. This makes the distance along axis D (the smallest cross-sectional dimension of sleeve 126) the maximum distance incision 128 is distended, while placing the largest cross-sectional dimension of sleeve 126 along the length of incision 126. In this manner, sleeve 126 occupies a greater portion of the cross-section of the distended incision, with attendant benefits in limiting leakage of infusion fluid.

It has been noted that thermal damage to tissue through which an incision is made is caused most frequently in areas 144, 146 as seen in FIG. 22. To alleviate this situation, a pair of longitudinally extending external ridges 148, 150 are formed along the interior wall 152 of sleeve 126 and are preferably positioned to intersect the minor axis D. In this manner, the sleeve portion closest to areas 144, 146 is prevented from contacting the phacoemulsification needle 134 and transmitting thermal energy to the tissue.

Referring now to FIG. 23, a sectional view of a phacoemulsification sleeve 154 is shown, having a round cross-sectional configuration. A pair of externally formed ridges 156, 158 are formed on the exterior surface of sleeve 154 to occupy a portion of the corners 160, 162 formed by the distended incision 164. In this manner, as described above, leakage through distended incision 164 is minimized during phacoemulsification.

Referring now to FIG. 24, the numeral 166 identifies a phacoemulsification sleeve having a circular cross-sectional shape and as described in connection with FIG. 23, having a pair of longitudinally-extending ridges 168, 170 formed along the lateral sides thereof.

A pair of longitudinally extending internal ribs 172, 174 are formed generally equidistantly between ridges 168, 170 on inner surface 176 of sleeve 166 and are intended to prevent sleeve 166 from collapsing against phacoemulsification needle 178 at those positions likely to cause thermal damage as depicted in FIG. 22.

As seen in FIGS. 23 and 24, sleeves 154, 166, respectively, are inserted such that ridges 156, 158 and 168, 170, respectively, are positioned at the corners of the distended incisions 164, 180, respectively. In this manner, an increased amount of space formed by the distended incisions is filled minimizing the area available for leakage.

Each of the infusion port arrangements shown in the foregoing figures has advantages over the prior art sleeves. One advantage is a measurable increase in the amount of infusion liquid that can be injected through the various sleeves depicted herein. For example, use of the original microsleeve with two circular diametrically opposed ports has been used at a flow rate of 100 ml per minute. By adding a third port it has been found possible to increase that flow rate to as much as 113 ml per minute.

It is contemplated that other variations in port size, number and positioning may also be used. As a general rule, the stiffer the material used to form the sleeve, the more ports may be used. Stiffer material will keep the sleeve from collapsing during surgery and touching the needle or otherwise affecting the rate of flow of infusing liquid through the sleeve.

What is claimed is:

1. In an infusion sleeve for use with a phacoemulsification handpiece, said handpiece having a phacoemulsification needle extending from a handpiece body, said infusion sleeve of the type having a hollow flexible tubular body with an open end through which said needle is inserted and an open tip through which said needle protrudes, said handpiece having a pathway through which irrigating liquid passes, said sleeve communicating with said liquid pathway to allow said liquid to pass through said sleeve when said sleeve is mounted to said handpiece, the improvement comprising:
    said tubular body formed with an oval cross-sectional configuration; said cross-section having a major, or longer axis and a minor, or shorter axis;
    at least three infusion ports formed on said tubular body proximate said tip through which said irrigating liquid is discharged; and
    first and second internal ribs formed on and protruding above an interior surface of said sleeve,
    said internal ribs extending substantially parallel with and protruding toward said needle when said sleeve is mounted to said handpiece,
    one said internal rib positioned on said inner surface substantially where said minor axis and said inner surface meet,
said internal ribs being spaced apart from said needle.

2. In an infusion sleeve for use with a phacoemulsification handpiece, said handpiece having a phacoemulsification needle extending from a handpiece body, said infusion sleeve of the type having a hollow flexible tubular body with an open end through which said needle is inserted and an open tip through which said needle protrudes, said handpiece having a pathway through which irrigating liquid passes, said sleeve communicating with said liquid pathway to allow said liquid to pass through said sleeve when said sleeve is mounted to said handpiece, the improvement comprising:
    at least three infusion ports through which said irrigating liquid is discharged,
    said ports formed on said tubular body proximate said tip; and
    a plurality of internal ribs formed on and protruding above an interior surface of said sleeve,
    said internal ribs extending substantially parallel with and protruding toward said needle when said sleeve is mounted to said handpiece
    said internal ribs being spaced apart from said needle.

3. The apparatus as recited in claim 2 wherein said sleeve has three said internal ribs.

4. The apparatus as recited in claim 3 wherein said three internal ribs are equidistantly spaced about said inner surface.

5. The apparatus as recited in claim 2 wherein said sleeve has four said internal ribs.

6. The apparatus as recited in claim 5 wherein said four internal ribs are equidistantly spaced about said inner surface.

7. The apparatus as recited in claim 2 wherein said sleeve has a round cross-sectional configuration;
    first and second ridges formed externally on and protruding above an exterior surface of said sleeve,
    said external ridges positioned substantially 180° apart and extending substantially parallel with said needle when said sleeve is mounted to said handpiece; and
    a plurality of internal ribs formed on and protruding above an interior surface of said sleeve,
    said internal ribs extending substantially parallel with and protruding toward said needle when said sleeve is mounted to said handpiece.

8. The apparatus as recited in claim 7 wherein
    first and second of said internal ribs are formed on said sleeve,
    said first internal rib positioned on said inner surface spaced substantially 180° from said second internal rib and spaced substantially 90° from said first external ridge.

9. The apparatus as recited in claim 2 wherein said sleeve is formed with an oval cross-sectional configuration, said cross-section having a major, or longer axis and a minor, or shorter axis;
    at least a pair of internal ribs formed on and protruding above an interior surface of said sleeve,
    said internal ribs extending substantially parallel with and protruding toward said needle when said sleeve is mounted to said handpiece,
    one said internal rib positioned on said interior surface substantially where said minor axis and said interior surface meet.

10. In an infusion sleeve for use with a phacoemulsification handpiece, said handpiece having a phacoemulsification needle extending from a handpiece body, said infusion sleeve of the type having a hollow flexible tubular body with an open end through which said needle is inserted and an open tip through which said needle protrudes, said handpiece having a pathway through which irrigating liquid passes, said sleeve communicating with said liquid pathway to allow said liquid to pass through said sleeve when said sleeve is mounted to said handpiece, the improvement comprising:
    at least three infusion ports through which said irrigating liquid is discharged, said tubular body having a round cross-sectional configuration; and first and second external ridges formed externally on and protruding above an exterior surface of said sleeve, said ridges extending substantially parallel with said needle when said sleeve is mounted to said handpiece, said first external ridge positioned on said exterior surface substantially 180° from said second external ridge.

11. The apparatus as recited in claim 10 wherein said first internal rib is positioned on said interior surface substantially 180° from said second internal rib and said first internal rib is positioned substantially 90° from said first external ridge.

* * * * *